United States Patent
Isaacson et al.

(10) Patent No.: US 10,271,778 B2
(45) Date of Patent: Apr. 30, 2019

(54) LED CONTROL UTILIZING AMBIENT LIGHT OR SIGNAL QUALITY

(75) Inventors: Philip O. Isaacson, Chanhassen, MN (US); Josh D. Schilling, Eden Prairie, MN (US)

(73) Assignee: Nonin Medical, Inc., Plymouth, MN (US)

( * ) Notice: Subject to any disclaimer, the term of this patent is extended or adjusted under 35 U.S.C. 154(b) by 325 days.

(21) Appl. No.: 12/476,687

(22) Filed: Jun. 2, 2009

(65) Prior Publication Data

US 2009/0299675 A1    Dec. 3, 2009

Related U.S. Application Data

(60) Provisional application No. 61/058,390, filed on Jun. 3, 2008.

(51) Int. Cl.
*A61B 5/1455* (2006.01)
*A61B 5/00* (2006.01)

(52) U.S. Cl.
CPC ........ *A61B 5/14551* (2013.01); *A61B 5/7221* (2013.01); *A61B 5/7242* (2013.01); *A61B 2560/0209* (2013.01)

(58) Field of Classification Search
CPC . A61B 5/14551; A61B 5/7221; A61B 5/7242; A61B 2560/0209
USPC .......................................... 702/104; 600/323
See application file for complete search history.

(56) References Cited

U.S. PATENT DOCUMENTS

| | | | |
|---|---|---|---|
| RE33,643 E * | 7/1991 | Isaacson | 128/633 |
| 5,190,632 A * | 3/1993 | Fujimiya et al. | 204/608 |
| 5,786,582 A * | 7/1998 | Roustaei et al. | 235/462.07 |
| 5,815,410 A * | 9/1998 | Heinke et al. | 702/135 |
| 5,995,859 A * | 11/1999 | Takahashi | 600/323 |
| 6,729,543 B1 * | 5/2004 | Arons | G06F 17/30017 235/462.01 |
| 6,905,834 B1 * | 6/2005 | Simpson et al. | 435/7.32 |
| 6,912,413 B2 * | 6/2005 | Rantala et al. | 600/322 |
| 7,026,627 B2 * | 4/2006 | Fowler et al. | 250/394 |
| 7,460,248 B2 * | 12/2008 | Kurtz et al. | 356/521 |
| 2001/0030686 A1 * | 10/2001 | Young, Jr. | H04N 1/00267 348/96 |
| 2001/0038450 A1 * | 11/2001 | McCaffrey | G01N 21/763 356/311 |
| 2003/0069486 A1 * | 4/2003 | Sueppel et al. | 600/322 |
| 2009/0259116 A1 * | 10/2009 | Wasserman et al. | 600/323 |

* cited by examiner

*Primary Examiner* — Alexander Satanovsky
(74) *Attorney, Agent, or Firm* — Schwegman Lundberg & Woessner, P.A.

(57) ABSTRACT

A system and method for controlling a light emitting device for an optical sensor based on signal quality and/or power consumption requirements. Drive current and/or integration time is controlled as a function of detected ambient light or signal quality. As the signal quality decreases the drive current or integration time can be adjusted to provide a more usable signal. If after some criteria for reduction, such as "time on" or high signal quality, then the drive current can be decreased.

34 Claims, 6 Drawing Sheets

LED CONTROL UTILIZING AMBIENT LIGHT OR SIGNAL QUALITY

CLAIM OF PRIORITY

The present application claims the benefit under 35 U.S.C. 119(e) of U.S. Provisional Patent Application Ser. No. 61/058,390, filed Jun. 3, 2008, which is incorporated herein by reference in its entirety.

TECHNICAL FIELD

The present invention relates to a method and apparatus for controlling and power consumption in medical devices and, in particular, for reducing power consumption in medical devices, such as blood oximetry devices, employing transmitted or reflected signals or both in combination to measure biological or environmental parameters of a patient or to communicate information pertaining thereto. More particularly, the present invention relates to a method and apparatus utilizing ambient light or signal quality to optimize power requirements of a device.

BACKGROUND OF THE INVENTION

There exists a wide range of devices that depend upon the transmission of signals to monitor or measure various biological or environmental parameters of a patient. For example, various forms of blood oximetry devices employ the transmission and reception of signals in the measurement of one or more biological or environmental parameters of a patient.

Blood oximetry devices are commonly used to monitor or measure the oxygen saturation levels of blood in a body organ or tissues, including blood vessels, or the oxidative metabolism of tissues or organ. These devices are also often capable of and are used to determine pulse rate and volume of blood flow in organs or tissues, or to monitor or measure other biological or environmental parameters.

As is well known to those of skill in the arts, blood oximetry devices measure the levels of the components of one or more signals of one of more frequencies as transmitted through or reflected from tissue or an organ to determine one or more biological or environmental parameters, such as blood oxygenation level and blood volume or pulse rate of a patient.

Blood oximetry devices may also be constructed as directly connected devices, that is, devices that are directly connected to a patient and that directly present the desired information or directly record the information and as remote devices, that is, devices attached to a patient and transmitting the measurements to a remote display, monitoring or data collection device.

Blood oximetry devices measure blood oxygen levels, pulse rate and volume of blood flow by emitting radiation in a frequency range, such as the red or near infrared range, wherein the transmission of the radiation through or reflectance of the radiation from the tissues or organ is measurably affected by the oxygen saturation levels and volume of the blood in the tissues or organ. A measurement of the signal level transmitted through a tissue or organ or reflected from a tissue or organ may then provide a measurement or indication of the oxygen saturation level in the tissue or organ. The transmitted or reflected signals may be of different frequencies which are typically affected in measurably different ways or amounts by various parameters or factors or components of the blood.

Parameters represented by transmitted or reflected signals may be represented by different and related or unrelated parameters of the received signals. For example, a signal transmitted through or reflected from tissue or an organ to measure, for example, blood oxygenation or flow, may have a constant or "dc" component due to the steady state volume of blood in the tissue or organ and a time varying or "ac" component indicative of the time varying volume of blood flowing through the tissue or organ due to the heart beat of the body. Each signal component may provide different information, and may provide information that may be used together to generate or determine yet other information.

Recent developments in medical devices, and in particular in medical monitoring and data collection or monitoring devices, such as blood oximeters, has been in the direction of smaller, lighter and more portable devices. Such "miniaturized" devices may be used, for example, for remote or portable use, such as by EMTs, or as individual user device. The development of such smaller and more portable devices, however, has meant greater reliance on smaller, more portable or more convenient power sources to drive the devices, such as batteries as opposed to connections to power lines. This trend has led to greater concerns regarding power consumption and battery life of the devices. For example, in a typical blood oximetry device or system, up to 75% or more of the power consumption of the device is used in driving the light sources, for example light emitting diodes (LEDs) or vertical-cavity surface-emitting lasers (VSCELs), generating the red or infrared signals that are transmitted through or reflected from the tissue or organ to measure the levels of oxygen in the tissue or organ.

BRIEF SUMMARY OF THE INVENTION

The present invention is directed to a system and method for optimizing power requirements of a light emitting device used for medical applications, such as measurement of patient oximetry parameter. A system of the present invention includes a light emitting device, a control unit for powering the light emitting device and responsive to a control signal for adjusting power applied to the light emitting device, the control signal being determined in response to a characteristic of a measured ambient light level and a signal associated with a physiological parameter measured using light produced by the light emitting device. In one example, the control signal may relate to drive current or on-time of LEDs or both. In another example, a measure of signal quality, such as the signal-to-noise ratio, may be used to optimize operation of the LEDs. In certain low light level applications, the signal-to-noise ratio is heavily influenced by shot noise and provides a useful parameter to minimize power consumption of the device.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

DETAILED DESCRIPTION OF THE INVENTION

Figure 1:
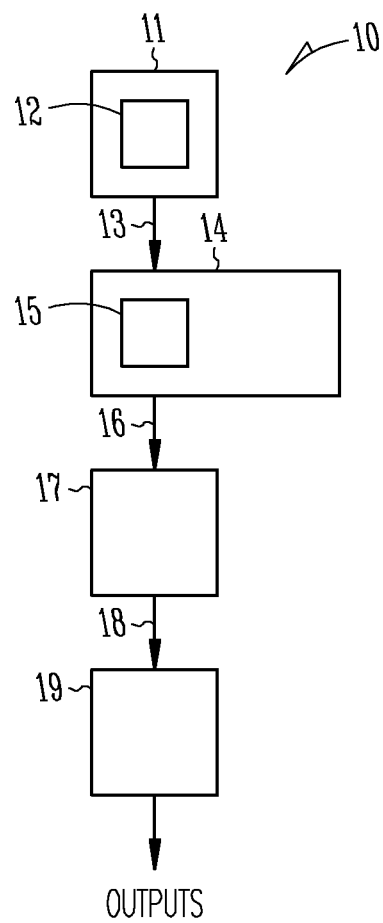
FIG. 1 is a diagrammatic illustration of a device using one or more signals transmitted through or reflected from tissue or an organ to measure or monitor a parameter of the tissue in which the present invention may be implemented.

By way of background, FIG. 1 is diagrammatic illustration of a device 10 using one or more signals transmitted through or reflected from tissue or an organ to measure or monitor a parameter of the tissue in which the present invention may be implemented. As discussed herein above, an example of such a device 10 may be a blood oximetry device, and a device 10 may be a self contained device or may be a part of a larger system that may include a plurality of devices 10 of different types.

Device 10 includes a light source 11 which contains one or more light emitters 12 for generating corresponding light signals 13. Light signals 13 are transmitted through or reflected from a tissue field, such as finger 14, an organ or other body parts having parameters 15 which are to be measured or monitored.

The light signals 13 that are transmitted through or reflected from the tissue field 14 are received as modulated signals 16 by sensors 17. Sensors 17 in turn provide received signals 18 that correspond to and represent modulated signals 16 and the components and characteristics of modulated signals 16 due to modulations and modifications imposed on or induced in emitted signals 13 due to parameters 15.

Received signals 18 contain information relating to parameters 15 of the tissue field 14, and that information can be extracted or otherwise obtained from received signals 18 by appropriate signal processing. Such processing may include, for example, comparing components of the received signals 18 with those of light signals 13 or detecting and extracting components of received signals 18, such as the "dc" and "ac" components of the signal or signals.

The processing of received signals 18 to obtain the desired information comprising or pertaining to parameters 15 is performed by a signal processor 19, which provides parameter outputs which may be displayed, stored for later display or subsequent processing, or transmitted to another facility or system.

The specific process and algorithms by which received signals 18 are processed to generate parameter outputs representing the desired information are dependent upon the specific parameters 15 and tissue fields 14 of interest. These factors, elements and processes are, however, well known to and understood by those of skill in the relevant arts and the adaptation of the present invention to different ones and different combinations of these factors, elements and processes will be well understood by those of skill in the relevant arts. As such, these elements need not and will not be discussed in further detail herein.

A significant potential reduction in power consumption of a device 10 could be realized by a reduction in the emitted power levels of emitted signals 13 as the power consumed by light emitters 12 often comprises 75% or even more of the power consumed by the device 10. However, the desired information in the signal may become buried in environmental and system noise or may otherwise may become degraded or distorted to the point of being useless or hazardous.

According to one aspect the present invention, the emitted intensity and/or on-time of emitted signals 13 may be reduced from their maximum or normal levels to some intermediate or relatively lower level so long as the "quality" of the signal components of interest of the corresponding received modulated signals 16 and received signals 18 are such that the parameter outputs may be extracted or otherwise obtained from the signal or signals with a level of reliability and a confidence level that is acceptable for purposes of the measurement or monitoring process. For purposes of the present invention, the "quality" of a given signal or the components of a signal are determined by signal characteristics such as the signal power level, amplitude or "intensity", or "signal-to-noise ratio".

According to one aspect the present invention, the signal processor 19 operates to maintain signal quality with a level of reliability and a confidence level that is acceptable for purposes of the measurement or monitoring process. In one example, aspects of an integration amplifier are controlled based on determined signal-to-noise ratios.

An embodiment of the present invention is directed to a system and method for monitoring a patient parameter or some other biological or physiological or chemical parameter by transmitting a monitoring signal from a signal source and to or through a target wherein the monitored parameter is a characteristic of the target. A modulated signal representing the emitted monitoring signal as modulated by the parameter is received by an appropriate sensor and the monitored parameter is determined from the characteristics of the modulated signal. In the particular, the present invention is directed to a method for controlling a signal characteristic of the emitted monitoring signal to control a characteristics of the emitted monitoring signal, such as the signal power or on-time, while insuring that the characteristics of the received modulated signal are such as to allow satisfactory determination of the monitored parameter.

Figure 2:
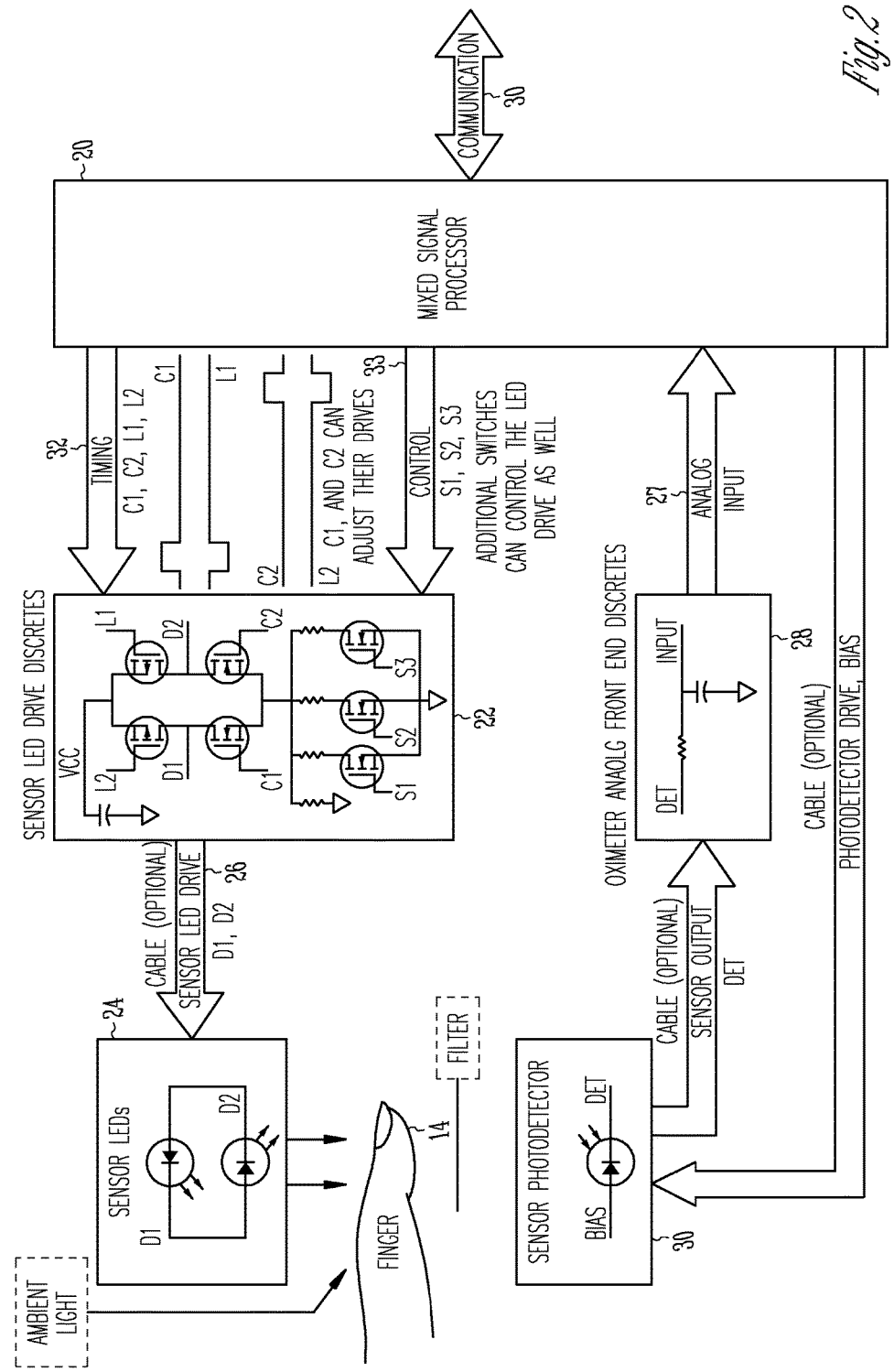
FIG. 2 is a diagrammatic representation of a preferred embodiment of the present invention utilizing a mixed signal processor to control LED drive discretes and sensor LEDs.

FIG. 2 is a diagrammatic representation of a preferred embodiment of the present invention utilizing a mixed signal processor 20 to control LED drive discretes 22 and sensor LEDs 24 via, for example, optional LED drive cable 26. Processor 20 also receives parameter signals 27 from analog front end discretes 28 as received from photodetector 30. Processor 20 may be in communication with another processor and/or remote device, via for example channel 31.

Processor 20 provides timing signal 32 and control signals 33 to sensor LED drive discretes 22.

In one embodiment of the present invention, processor 20 includes an application-specific-integrated-circuit (ASIC). Advantages of an ASIC-based device include significant cost savings as fewer discrete components are required, minimizing the opportunity of reverse engineering, reduced assembly and test time, increased flexibility of component placement, and potential power savings. In alternative embodiments, processor 20 may include a variety of analog and/or digital components as appreciated by one of ordinary skill in the art.

Figure 3:
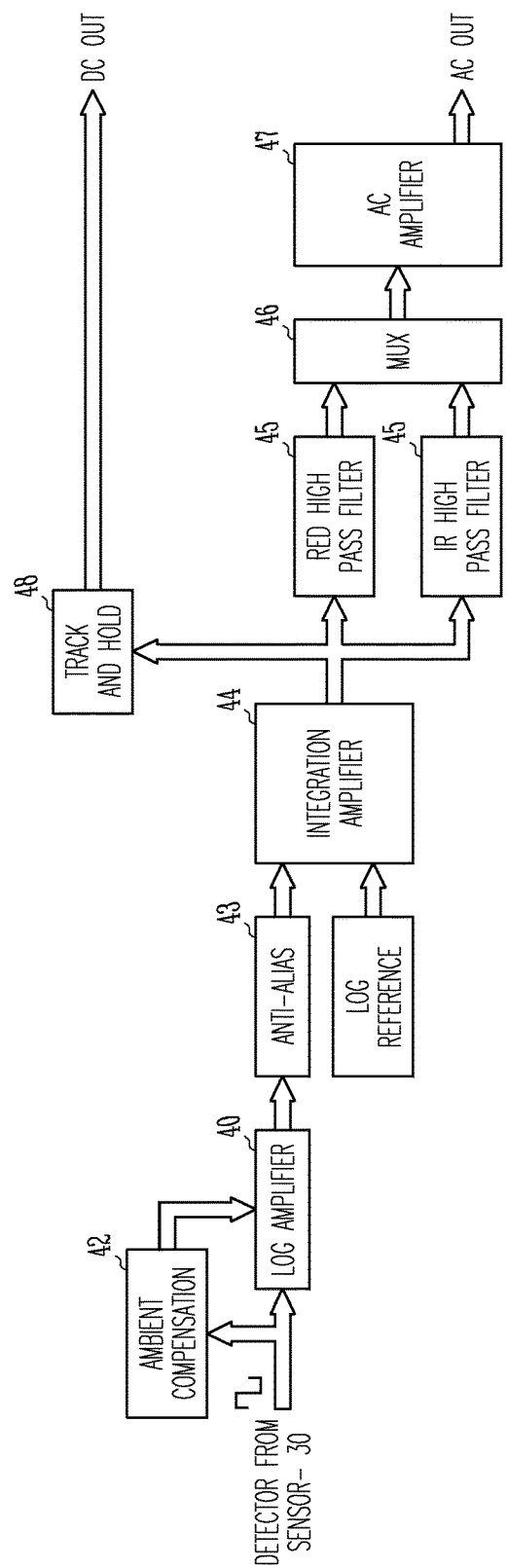
FIG. 3 is an illustration of a front end signal path of a device implementing the present invention.

FIG. 3 is an example of a front end signal path of a device implementing the present invention. The front end includes an input current-to-log amplifier 40, and ambient light current track/hold amplifier 42 together receiving an input signal from sensor 30. The front end signal path also includes an anti-alias filter 43, an integration amplifier 44, a dual channel high pass filter 45, a multiplexor 46, a voltage amplifier 47 and a track/hold DC voltage amplifier 48. Outputs of the front end include DC out and AC out.

Integration amplifier 44, which may include an op-amp and an integrating capacitor or switched capacitor, operates in a well known fashion to integrate an input signal. An implementation of an integrator circuit in a pulse oximeter is disclosed in U.S. Pat. Reissue No. 33,643, entitled "Pulse Oximeter With Circuit Leakage and Ambient Light Compensation", assigned to the present assignee, and incorporated by reference herein for all purposes.

Log amplifier 40 accepts an input signal (current) from photodetector 30 and outputs a logarithmic voltage representation of the input. The ambient light current amp 42 tracks and samples an ambient light measurement to provide ambient light compensation, as described hereinafter. In general, the signal captured by the photodetector 30 is not only dependent on the light absorption characteristics of the tissue field but also on the light absorption of the detector itself.

Figure 4:
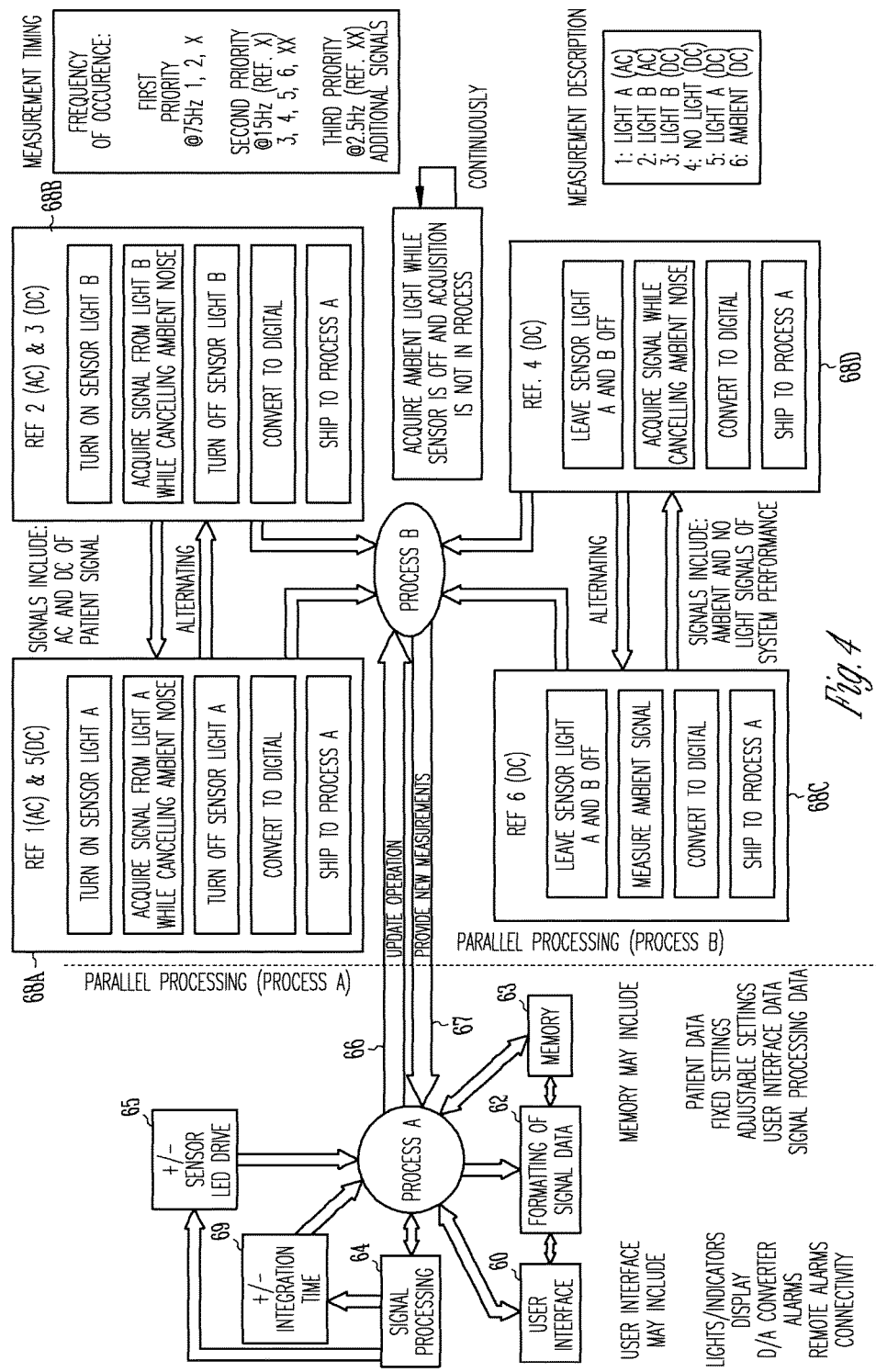
FIG. 4 is a functional block diagram of a device utilizing an embodiment of a compensation circuit of the present invention using ambient light levels and/or signal-to-noise ratios.

FIG. 4 depicts a functional block diagram of a device 10 utilizing an embodiment of a compensation circuit of the present invention using ambient light levels and/or signal-to-noise ratios. In this example, Processes A and B are parallel processes though alternative architectures to implement multiple processes may also be viable. Processes A and B may be implemented by processor 20, such as described above, or by separate processors. As such, Processes A and B may be implemented with a variety of hardware and/or software.

Process A includes user interface block 60, signal data formatting block 62, memory block 63, signal processing block 64. User interface block 60 may include one or more of lights and indicators, displays, D/A converter(s), alarms, connectivity options, etc. Memory block 63 may include, for example, patient data, fixed settings, adjustable settings, user interface data, and signal processing data. Signal processing block 64 directly or indirectly controls a sensor LED drive adjust block 65 and an integration time adjust block 69. LED drive adjust block 65 adjusts the LED drive current to increase or decrease the power requirements of the light emitters. Integration time adjust block 69 increases or decreases the integration time of integration amplifier 44. As described herein, both LED drive current and integration time may be controlled in response to signal quality and/or power consumption considerations.

Processes A and B are in communication with each other via lines 66, 67. As described in more detail hereinafter, line 66 represents communication relating to operation of Process B, such as instructions to update operation of Process B. Line 67 represents new measurement data for use by Process A. In a general sense, Process A monitors the quality of the signal received from Process B and controls among other tasks, an LED drive current and integration time.

Process B depicts four operational states 68A, 68B, 68C and 68D of a device 10 implementing an ambient light compensation feature of the present invention. A device processor is used to implement the methods of each operational state 68. In this example, Process B continually acquires ambient light measurements while the LEDs are off and data acquisition is not in process.

States 68A and 68B provide signals representing the AC and DC characteristics of the measure parameter. States 68C and 68D provide signals representing ambient and "no-light" characteristics of the device.

Process B is controlled to transition between the four operational states. In the example of FIG. 4, the operational states may be utilized to obtain measurements for communication to Process A. In this example, six measurements are defined as follows:

1. Light A On—AC
2. Light B On—AC
3. Light B On—DC
4. No-Light—DC
5. Light A On—DC
6. Ambient Light—DC It should be appreciated that the order and numbering of the operational states and measurements in this example are arbitrarily chosen and could be different in another implementation. Measurement 1—Light A (AC) includes the steps of turning sensor light A on, acquiring a signal from light A while cancelling ambient noise, turning sensor light A off, converting the acquired signal to digital form, and communicating the signal to Process A.

Measurement 2—Light B (AC) includes the steps of turning sensor light B on, acquiring a signal from light B while cancelling ambient noise, turning sensor light B off, converting the signal to digital form, and communicating the signal to Process A.

Measurement 3—Light B (DC) includes the steps of turning sensor light B on, acquiring a signal from light B while cancelling ambient noise, turning sensor light B off, converting the signal to digital form, and communicating the signal to Process A.

Measurement 4—No-Light (DC) includes the steps of leaving sensor lights A and B off, acquiring a signal while cancelling ambient noise, converting the signal into digital form, and communicating the signal to Process A.

Measurement 5: Light A (DC) includes the steps of turning sensor light A on, acquiring a signal from light A while cancelling ambient noise, turning sensor light A off, converting the acquired signal to digital form, and communicating the signal to Process A.

Measurement 6: Ambient (DC) includes the steps of turning sensor light A and B off, measuring an ambient light signal, converting the signal to digital form, and communicating the signal to Process A.

The timing of transitions between the operational states may be prioritized to adequately capture the faster-changing AC signal measurements. In one example, the measurements 1, 2 and X occur at 75 Hz. Measurement X represents measurements 3, 4, 5, 6, XX in series. Measurement xx represents additional signals, such as battery voltage, log ref voltage, Vcc and Vref. As a consequence, the slower transitioning DC measurements are sampled at a lower frequency.

Figure 5:
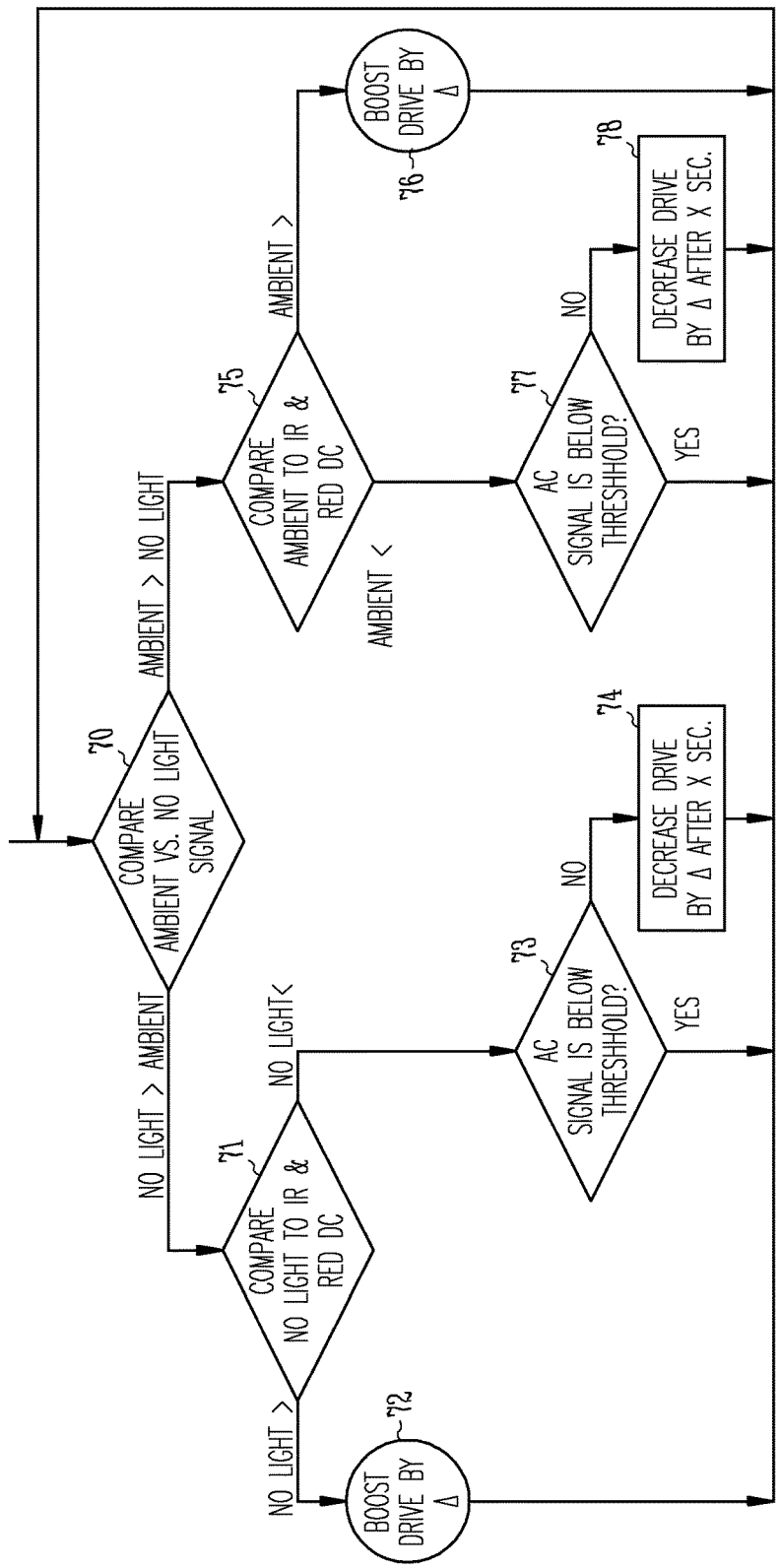
FIG. 5 is a flow chart depicting operation of a device incorporating an example of an ambient light level compensation system of the present invention.

FIG. 5 represents a flow chart depicting operation of a device 10 incorporating an example of an ambient light level compensation system of the present invention. At step 70, a comparison is made between an Ambient Light measurement and the No-Light measurement, taken in this example during Measurements 4 and 6 depicted in FIG. 4. If the No-Light measurement is greater than the Ambient Light measurement, the No-Light measurement is compared to IR and Red DC measurements at step 71. In this example, IR and Red DC correspond to Lights A and B of FIG. 4. If the No-Light measurement is greater than the IR and Red DC measurements, the LED drive current can be boosted by an amount, δ, as step 72. On the other hand, if the No-Light measurement is less than the IR and Red DC measurements, a determination of whether the AC light value is below a predetermined threshold is made at step 73. If the AC light value is not below the threshold value, the LED drive current can be reduced at step 74, preferably after x seconds.

Figure 6:
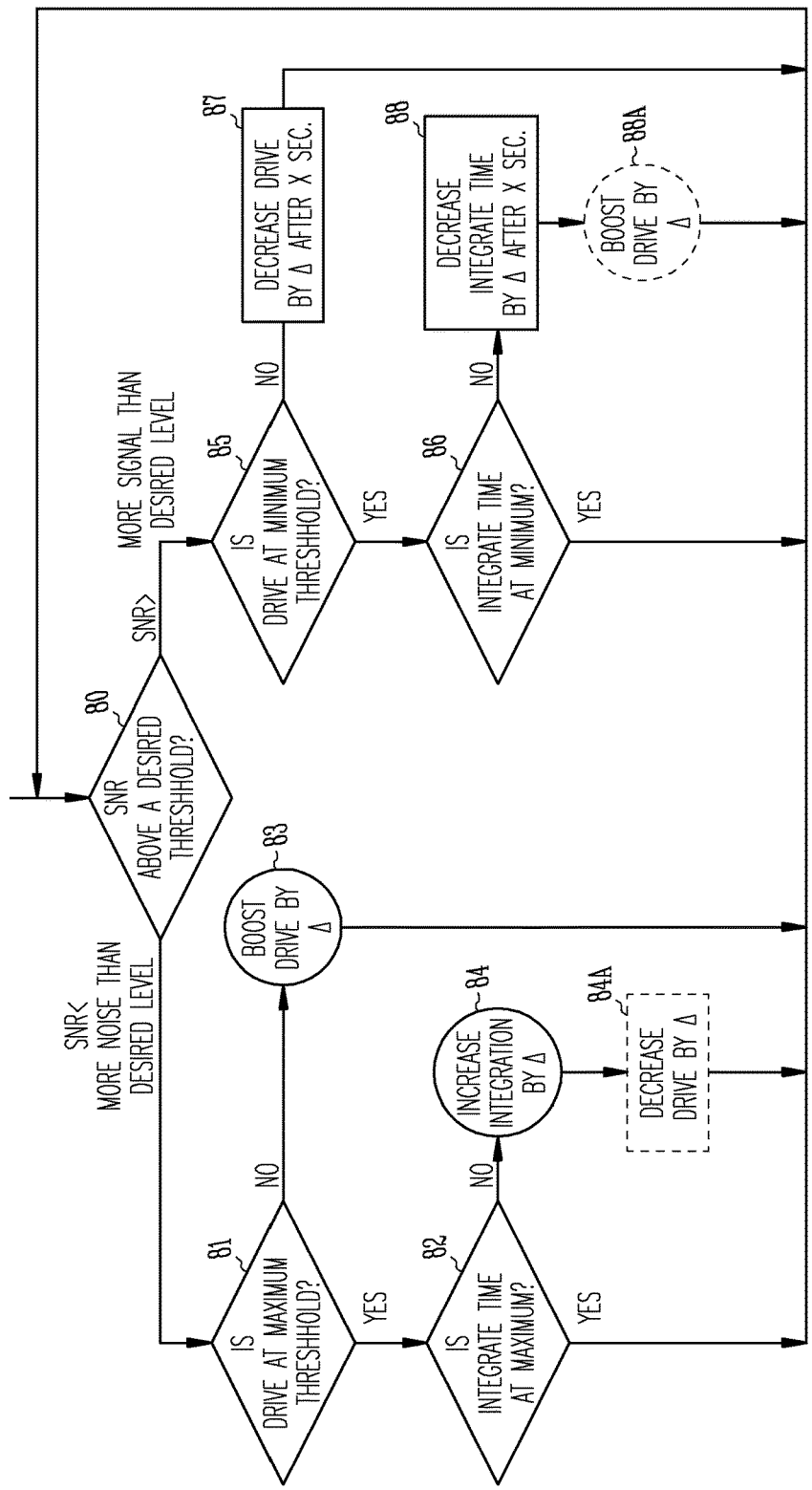
FIG. 6 is a flow chart depicting operation of one embodiment of device.

If the Ambient Light measurement is greater than the No-Light measurement at step 71, a comparison is made at step 75 between the Ambient Light measurement and the IR and Red DC measurements. If the Ambient Light measurement is greater than then IR and Red DC measurements, the LED drive current can be increased by an amount, δ, at step 76. On the other hand, if the Ambient Light measurement is less than the IR & Red DC measurements, a comparison is made at step 77 to determine whether the AC light signal is below a predetermined threshold. If the AC light signal is not less than the threshold value, the LED drive current can be reduced at step 78, preferably after x seconds. In a general sense, FIG. 5 depicts optimization of LED drive current while maintaining the quality of the AC signal. In comparison, FIG. 6 depicts optimizing integration times while maintaining a parameter representative of signal quality, such as signal-to-noise ratio.

There are two dominant noise sources in high speed photodetectors: shot (or quantum) noise, and electronic noise. Shot noise is an intrinsic property of the light itself, rather than the detector. A variety of different sources contribute to electronic noise including, but not limited to, thermal fluctuations and circuit flicker.

Shot noise occurs when the finite number of particles that carry energy, such as electrons in an electronic circuit or photons in an optical device, is small enough to give rise to detectable statistical fluctuations in a measurement. Shot noise is present in photodetectors due to the random arrival rate of photons from the light source(s) and the random recombination of charge carriers within the photodetector. As described below, at low light levels the signal quality is heavily influenced by shot noise.

The power consumption of device 10 may be minimized by using a relatively weak optical signal. However, detection of weak optical signals requires that the photodetector and its following amplification circuitry be optimized for a desired signal-to-noise ratio, SNR. Obviously, one way to achieve a higher SNR is to increase the transmitted power, for example, by increasing LED drive current. Because the signal power increases quadratically with increasing optical power, while the shot noise of the detector increases only linearly, increasing the transmitting power will always increase the SNR. However, an increase in transmit power comes at the expense of increased power consumption, which may be important in certain low power detector applications.

It can be seen that shot noise becomes more important when the number of photons collected is small. The intensity of a light source will yield the average number of photons collected, but knowing the average number of photons which will be collected will not give the actual number collected. The actual number collected will be more than, equal to, or less than the average, and their distribution about that average will be a Poisson distribution. Since the Poisson distribution approaches a normal distribution for large numbers, the shot noise in a signal will approach a normal distribution for large numbers of photons collected. The standard deviation of the shot noise is equal to the square root of N, the average number of photons. As a result, the signal-to-noise ratio is a function of N, the average number of photons collected. When N is very small, the signal-to-noise ratio is very large as well.

For certain low power applications, the signal-to-noise ratio can be used to optimize device 10 performance. FIG. 6 illustrates one example of a process useful in such application.

FIG. 6 is a flow chart depicting operation of one embodiment of device 10. FIG. 6 illustrates a process for optimizing integration times (and optionally drive current) while maintaining a desired signal-to-noise ratio (SNR). At step 80, a comparison is made between a calculated or determined SNR and a predetermined threshold SNR value. If the calculated SNR is lower than a desired threshold value, then the LED drive current is evaluated at step 81. If the LED drive current is at a maximum threshold, then evaluation of integration time occurs at step 82. If the integration time is less than a maximum time period, then the integration time can be incrementally increased at step 84. The LED drive current may be decreased at optional step 84a. In one example, a combination of incremental adjustments to integration time and LED drive current is utilized with reference to a look-up table, algorithm or other equation. The incremental changes to integration time may be a function of the measured SNR or another signal parameter. For example, a greater difference between SNR and desired SNR may warrant an greater incremental adjustment to integration time as compared to a smaller difference. At step 81, if the LED drive current is not at a maximum threshold, then the LED drive boost may be incrementally increased at step 83.

At step 80, if the determined SNR is greater than a desired SNR, then evaluation of the LED drive current is made at step 85. If the drive current is greater than a minimum threshold, then the drive current can be decreased at step 87. On the other hand, if the drive current is at a minimum threshold, then an evaluation of integration time occurs at step 86. If the integration time is greater than a minimum time period, the integration time can be incrementally decreased at step 88. Optionally, the LED drive current may be incrementally increased at step 88a. In this context, the SNR can be periodically evaluated and compared to a desired SNR threshold in order to optimize the integration times and/or LED drive current to, for example, minimize the power consumption of device 10.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps.

What is claimed is:

1. A device for measuring oxygen saturation, the device comprising:
a sensor having a light emitter and having a detector configured to provide an output corresponding to an optical property of tissue using light from the emitter;
an integration amplifier coupled to the sensor, the integration amplifier having a controllable integration time;
a processor coupled to the sensor and configured to determine a value corresponding to a signal to noise ratio for the output and configured to compare the value with a threshold and further wherein the processor is configured to compensate for ambient light using a plurality of operational states for the sensor, and wherein the operational states include a first state in which a first light of the emitter is powered on, a second state in which a second light of the emitter is powered on, and a third state in which the first light and the second light are powered off, and wherein the value is determined based on measurements during the first state, the second state and the third state; and
a control unit coupled to the processor and coupled to the integration amplifier, the control unit configured to adjust power supplied to the sensor based on the comparison and control the integration time based on the comparison, wherein controlling the integration time based on the comparison comprises incrementally increasing the integration time when the integration time is less than a maximum time period and incrementally decreasing the integration time when the integration time is greater than a minimum time period.

2. The device of claim 1 wherein the emitter is configured to emit light having at least one of a near infrared range and a red range.

3. The device of claim 1 wherein the emitter includes at least one of a light emitting diode and a vertical-cavity surface-emitting laser (VCSEL).

4. The device of claim 1 wherein the processor is configured to determine a measure of ambient noise.

5. The device of claim 1 wherein the processor is configured to determine a measure of shot noise.

6. The device of claim 1 wherein the processor is configured to determine a measure of electronic noise.

7. The device of claim 1 wherein the processor is configured to determine a measure of at least one of thermal fluctuations and circuit flicker.

8. The device of claim 1 wherein the control unit is configured to adjust power by adjusting intensity of the emitted light.

9. The device of claim 1 wherein the control unit is configured to adjust power by adjusting a time of the emitted light.

10. The device of claim 1 wherein the control unit is configured to adjust power by adjusting an acquisition time of the detector.

11. The system of claim 1 wherein adjusting the power supplied to the sensor and controlling the integration time further include adjusting the power supplied to the sensor and increasing or decreasing the integration time based on values obtained from a look-up table.

12. A method for measuring oxygen saturation, the method comprising:
emitting light from a device having a sensor, the device configured to measure a parameter of a tissue using an optical property of the tissue, the light emitted from an emitter of the sensor;
measuring a light signal using a detector of the sensor, the light signal corresponding to the emitted light;
using a processor to determine a value corresponding to a signal to noise ratio for the light signal, wherein the processor is configured to compensate for ambient light using a plurality of operational states for the sensor, and wherein the operational states include a first state in which a first light of the emitter is powered on, a second state in which a second light of the emitter is powered on, and a third state in which the first light and the second light are powered off, and wherein the value is determined based on measurements during the first state, the second state and the third state;
comparing the value with a threshold; and
adjusting power consumption of the device based on the comparison and adjusting an integration time of an integration amplifier of the device, wherein adjusting the integration time based on the comparison comprises incrementally increasing the integration time when the integration time is less than a maximum time period and incrementally decreasing the integration time when the integration time is greater than a minimum time period.

13. The method of claim 12 wherein emitting light includes emitting radiation in at least one of a near infrared range and a red range.

14. The method of claim 12 wherein emitting light includes emitting using at least one of a light emitting diode and a vertical-cavity surface-emitting laser (VCSEL).

15. The method of claim 12 wherein measuring the light signal includes generating a signal using a light detector.

16. The method of claim 12 wherein using the processor to determine the value includes measuring ambient noise.

17. The method of claim 12 wherein using the processor to determine the value includes measuring shot noise.

18. The method of claim 12 wherein using the processor to determine the value includes measuring electronic noise.

19. The method of claim 12 wherein measuring electronic noise includes measuring at least one of thermal fluctuations and circuit flicker.

20. The method of claim 12 wherein adjusting power consumption includes adjusting intensity of the emitted light.

21. The method of claim 12 wherein adjusting power consumption includes adjusting a time of the emitted light.

22. The method of claim 12 wherein adjusting power consumption includes adjusting an acquisition time for measuring the parameter.

23. A system comprising:
an emitter configured to emit light;
a detector coupled to an integration amplifier and configured to provide an output corresponding to a measured light signal based on an optical property of tissue and the emitted light, the integration amplifier having a controllable integration time, the emitter and the detector defining a sensor;
a processor coupled to the detector and configured to determine a value corresponding to a measure of quality of the light signal and configured to compare the value with a threshold, wherein the processor is configured to compensate for ambient light using a plurality of operational states for the sensor, and wherein the operational states include a first state in which a first light of the emitter is powered on, a second state in which a second light of the emitter is powered on, and a third state in which the first light and the second light are powered off, and wherein the value is determined based on measurements during the first state, the second state and the third state; and a control unit coupled to the integration amplifier and configured to adjust power consumption based on the comparison and configured to control the integration time based on the comparison, wherein controlling the integration time based on the comparison comprises incrementally increasing the integration time when the integration time is less than a maximum time period and incrementally decreasing the integration time when the integration time is greater than a minimum time period.

24. The system of claim 23 wherein the measure of quality includes at least one of signal power level, signal amplitude, and signal to noise ratio.

25. The system of claim 23 wherein the emitter is configured to emit light having at least one of a near infrared range and a red range.

26. The system of claim 23 wherein the emitter includes at least one of a light emitting diode and a vertical-cavity surface-emitting laser (VCSEL).

27. The system of claim 23 wherein the processor is configured to receive a measure of ambient noise.

28. The system of claim 23 wherein the processor is configured to receive a measure of shot noise.

29. The system of claim 23 wherein the processor is configured to receive a measure of electronic noise.

30. The system of claim 23 wherein the processor is configured to receive a measure of at least one of thermal fluctuations and circuit flicker.

31. The system of claim 23 wherein the control unit is coupled to at least one of an amplifier and a driver.

32. The system of claim 31 wherein the driver is coupled to the light emitter.

33. The system of claim 32 wherein the control unit is configured to adjust power supplied to the driver.

34. The system of claim 23 wherein the control unit is configured to adjust power by adjusting an acquisition time of the emitted light.

* * * * *